United States Patent [19]

Himes

[11] Patent Number: 5,948,947
[45] Date of Patent: Sep. 7, 1999

[54] ALKYLATION PROCESS WITH SEPARATE REJECTION OF LIGHT AND HEAVY ACID SOLUBLE OILS

[75] Inventor: James F. Himes, Mount Prospect, Ill.

[73] Assignee: Uop LLC, Des Plaines, Ill.

[21] Appl. No.: 08/927,004

[22] Filed: Sep. 10, 1997

Related U.S. Application Data

[60] Provisional application No. 60/026,282, Sep. 18, 1996.

[51] Int. Cl.⁶ .................... C07C 2/58; C07C 7/00
[52] U.S. Cl. .............. 585/724; 585/721; 585/723; 585/725; 585/802
[58] Field of Search .................... 585/721, 723, 585/724, 725, 802

[56] References Cited

U.S. PATENT DOCUMENTS

| | | | |
|---|---|---|---|
| 4,237,327 | 12/1980 | Winter, III | 585/450 |
| 4,237,328 | 12/1980 | Winter, III | 585/456 |
| 5,073,674 | 12/1991 | Olah | 585/725 |
| 5,191,150 | 3/1993 | Child et al. | 585/809 |
| 5,382,746 | 1/1995 | Child et al. | 585/802 |
| 5,763,728 | 6/1998 | Kocal et al. | 585/724 |

FOREIGN PATENT DOCUMENTS

| | | | |
|---|---|---|---|
| 57-92502 | 6/1982 | Japan | C01B 7/19 |

*Primary Examiner*—Glenn A. Caldarola
*Assistant Examiner*—In Suk Bullock
*Attorney, Agent, or Firm*—Thomas K. McBride; John G. Tolomei; Michael A. Moore

[57] ABSTRACT

An HF-agent complex, such as HF-pyridine complex where the complexing agent is pyridine, is recovered and recycled from a by-product stream containing ASO, and ASO is rejected from the by-product stream, in an alkylation process using the complex.

15 Claims, 1 Drawing Sheet

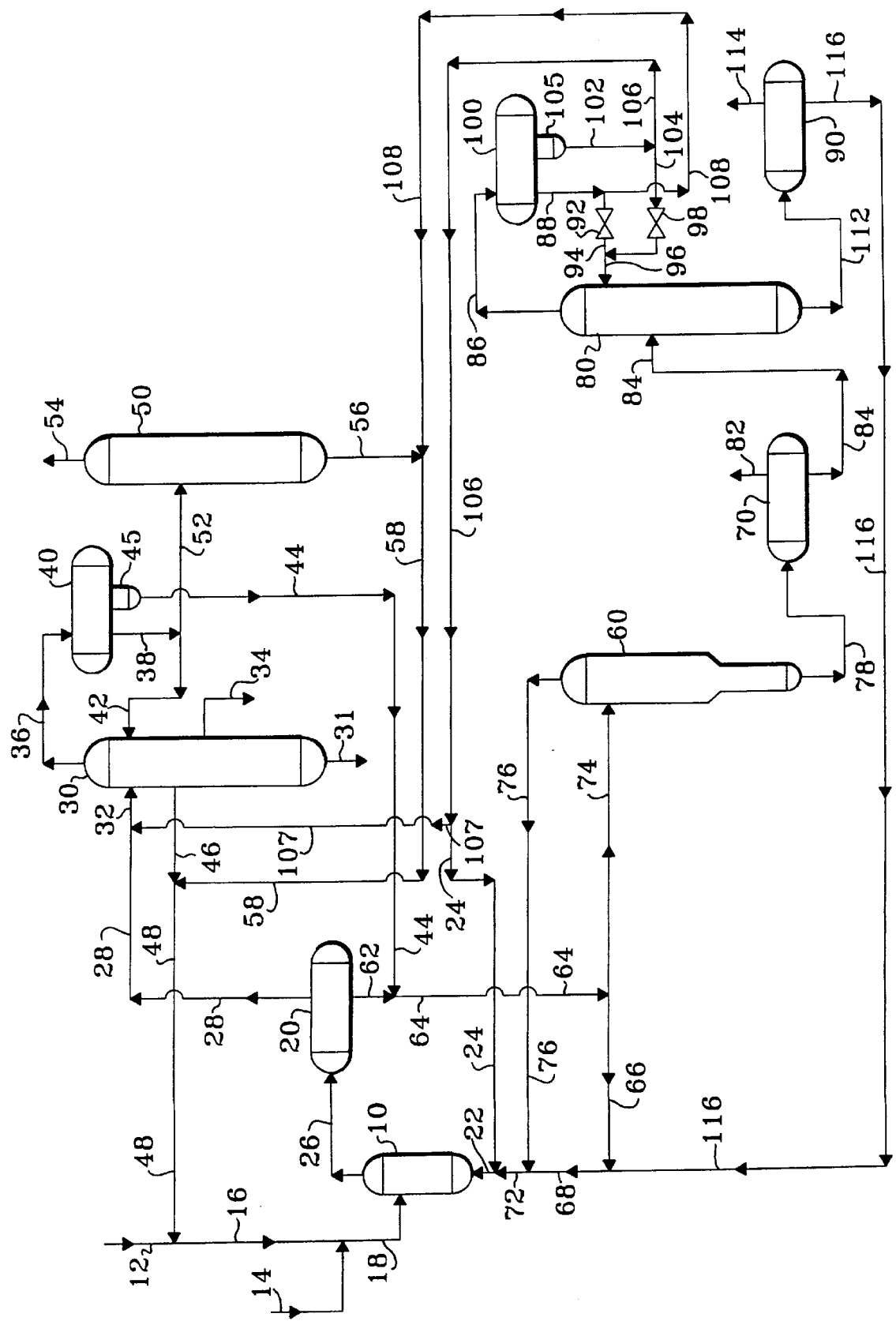

ALKYLATION PROCESS WITH SEPARATE REJECTION OF LIGHT AND HEAVY ACID SOLUBLE OILS

CROSS-REFERENCE TO RELATED APPLICATION

This application claims the benefit of U.S. Provisional Application No. 60/026,282, filed on Sep. 18, 1996.

FIELD OF THE INVENTION

The field of the present invention is hydrocarbon processing. The invention generally relates to catalyst alkylation of hydrocarbons employing liquid hydrogen fluoride (HF).

BACKGROUND OF THE INVENTION

Alkylation using HF is a widely used commercial refining and petrochemical process. Generally, alkylation is the addition of an alkyl group to another hydrocarbon. Commercially, HF is used to alkylate isobutane with propylene, butylene, and amylene isomers to produce high octane gasoline blending components, as well as to alkylate benzene in the manufacture of detergents.

The commercial process for alkylating isobutane with propylene is typical of many commercial HF alkylation process. Briefly, propylene and a stoichiometric excess of isobutane contact HF in a reactor where alkylation reactions produce alkylate. The reactor effluent passes to a settler in which the effluent separates into an acid phase containing HF and a hydrocarbon phase containing unreacted isobutane and alkylate. The acid phase is recycled to the reactor. The hydrocarbon phase passes to a fractionation column, commonly called an isostripper or a deisobutanizer, from which the isobutane is also recycled to the reactor and alkylate is recovered as product.

In addition to producing alkylate, HF alkylation processes also produce a by-product called acid-soluble oil, or ASO, which is soluble in HF. ASO is a recognized term in the art of alkylation, and is sometimes referred to as HF-soluble oil, polymer, conjunct polymer, or polymer by-product. Because ASO is soluble in HF, ASO in the settler concentrates not in the hydrocarbon phase but in the acid phase, and consequently the ASO is recycled to the reactor. In the reactor, ASO generally decreases the catalytic activity of the HF. While this effect can be beneficial at relatively low concentrations of ASO, if allowed to accumulate to relatively high concentrations ASO has a detrimental effect on the process. For this reason, ASO is typically removed at least periodically from a slip stream of the acid phase by a process that is commonly called regeneration.

Regeneration is typically performed in two ways, internal regeneration and external regeneration. In internal regeneration, a slip stream of the acid phase, which is hereinafter referred to as a by-product stream, remixes with the hydrocarbon phase and passes to the isostripper. The ASO, being a heavy polymerized by-product, tends to pass downward in the isostripper and is rejected from the bottom of the isostripper and out of the process. The HF that enters the isostripper in internal regeneration tends to pass upward in the isostripper, is recovered from the overhead of the isostripper, and is recycled to the reactor. External regeneration, on the other hand, uses a stripping column commonly called an external regenerator to remove ASO from a by-product stream of the acid phase. In an external regenerator, either heat or isobutane or both strip HF overhead, leaving a residue of mostly ASO which is rejected from the bottom of the external regenerator and out of the process. The overhead of the external regenerator either is recycled as a condensed liquid to the reactor or is passed as a vapor to the isostripper where it may be used to assist in fractionation.

A growing and recent trend in HF alkylation processes is the use of complexing agents to minimize the volatility of the acid phase. Because HF is volatile and the environmental risks arising from an accidental release of HF to the atmosphere are more and more undesirable, complexing agents that reduce the vapor pressure of HF and the tendency of HF to form an aerosol are now in greater use than ever before. Complexing agents typically contain at least one Lewis base site, which commonly comprises a Group 5A element such as nitrogen. Certain nitrogen-containing compounds, such as pyridine, picolines, quinoline, trimethylamine, and triethylamine, are known to form complexes with HF to reduce its volatility. For example, see Japanese Patent Disclosure No. 57(1982)-92502 (Oda et al). U.S. Pat. No. 5,073,674 (Olah) discloses that mixtures of HF and preferred nitrogen-containing compounds (complexing agents) such as ammonia, methylamines, ethylamines, propylamines, butylamines, pentylamines, pyridine, picolines, melamine, and hexamethylene-tetramine remained effective catalysts in alkylation of alkanes by alkenes. Mixtures of Olah's preferred complexing agents with HF are hereinafter referred to as HF-amine complexes.

A problem that arises with the use of some complexing agents in HF alkylation processes is that both internal and external regeneration tend to reject not only ASO but also the HF-agent complex from the process. As a solution to this problem, a two-step method for removing ASO from a by-product stream containing HF, ASO, and HF-agent complex, where the complexing agent contains at least one Lewis base site containing a Group 5A element and the by-product stream has a molar ratio of HF per Lewis base site substantially above 5:1, is practiced in the art. First, a portion of the HF in the by-product stream is selectively removed to produce an HF-depleted stream having a molar ratio of HF per Lewis base site of 3:1 to 5:1. Then, the HF-depleted stream is separated into a hydrocarbon phase enriched in ASO and an acid phase depleted in ASO that contains a substantial portion of the HF-agent complex. The selectively removed HF and the acid phase are both recycled to the hydrocarbon alkylation step, and the hydrocarbon phase is rejected from the process. Thus, this method rejects ASO but not HF-agent complex from the process.

One of the problems with the method described in the previous paragraph is that the HF-enriched stream that contains the selectively removed HF also contains 10 to 15 wt-% ASO. The ASO in the HF-enriched stream tends to be lighter than the heavier ASO that remains in the HF-depleted stream and which is ultimately rejected from the process in the hydrocarbon phase. Nevertheless, like the heavy ASO, this light ASO which is recycled to the alkylation reactor has a detrimental effect on the alkylation reactions. Thus, a method is sought for rejecting ASO, in particular light ASO, from an HF alkylation process that uses an HF-agent complex, wherein the complexing agent contains at least one Lewis base site containing a Group 5A element.

U.S. Pat. No. 5,073,674 (Olah) discloses a process of alkylating aliphatic hydrocarbons with alkenyl hydrocarbons in the presence of liquid HF-ammonia or HF-amine complexes.

U.S. Pat. No. 5,191,150 (Child et al.) discloses a method of separating a stream containing ASO, HF, and sulfolane by first separating out HF and then gravitationally separating the HF-depleted stream into a polymer-rich stream and a sulfolane-rich stream.

U.S. Pat. No. 5,382,746 (Child et al.) discloses an HF alkylation process comprising passing a reactor effluent settler acid phase containing sulfolane, ASO, and HF to an external regenerator; passing the external regenerator overhead stream containing HF and light ASO to an isostripper; recycling an isostripper overhead stream containing HF to the alkylation reactor; and recovering an isostrpper bottom stream containing alkylate and light ASO.

In motor fuel alkylation processes, the passage of the overhead vapor stream of an external regenerator to an isostripper, wherein the overhead vapor stream enters the isostripper at an intermediate point that is below the feed point of the isostripper, is practiced commercially.

The regeneration of HF used as catalyst is also practiced in the production of detergents by the reaction of $C_8$-plus normal olefinic hydrocarbons and benzene. The use in such a process of an external regenerator for regenerating HF and of another stripping column, which is called an HF stripper, for separating HF from the hydrocarbon-containing reactor effluent phase is shown in U.S. Pat. Nos. 4,237,327 (Winter, III) and 4,237,328 (Winter, III). U.S. Pat. No. 4,237,327 teaches a process in which an overhead vapor stream having a low concentration of ASO exits an external regenerator and enters an HF stripper at an upper intermediate point that is below the feed point of the HF stripper. U.S. Pat. No. 4,237,328 teaches passing the overhead vapor stream of an external regenerator and the overhead vapor stream of an HF stripper to a common single overhead condenser.

SUMMARY OF THE INVENTION

This present invention is a process for recovering an HF-agent complex from a hydrocarbon alkylation by-product stream containing acid soluble oil (ASO), HF, and HF-agent complex. The complexing agent contains a Lewis base site that comprises a Group 5A element, preferably nitrogen. The process first removes at least some of the HF and the ASO from the by-product stream to form an HF-depleted stream containing ASO, HF, and HF-agent complex and an HF-enriched stream containing ASO and HF, and then separates the HF-enriched stream in the alkylate product fractionator. The HF-depleted stream is separated into a phase enriched in ASO and another phase enriched in the HF-agent complex. This process is a particularly effective method of removing ASO from a mixture in which a Lewis base such as Olah's preferred complexing agents is used to reduce the tendency of HF to form an aerosol.

The surprising recognition that has been made is that simultaneous removal from the by-product stream of both HF and ASO is an effective method of separating ASO from HF and HF-agent complex, despite the fact that it is necessary to remove only HF in order to subsequently use phase separation to separate ASO from the HF-agent complex. In addition, prior to this invention persons of ordinary skill in the art believed that separating the by-product stream, which is a single ASO-containing stream, into two ASO-containing streams constituted a backward step rather than a forward step toward the goal of separating ASO from HF and HF-agent complex. This invention uses that apparently backward step as the first step in separating ASO from the by-product stream, and then by using the alkylate product fractionator and phase separation achieves an even better separation of ASO from the mixture of ASO, HF, and HF-agent complex than prior art process.

As mentioned in the previous paragraph, one of the reasons why the results of the present invention are unexpected is because persons of ordinary skill in the art know that removal of only HF from the by-product stream is sufficient to facilitate the subsequent phase separation of ASO from the HF-agent complex. In mixtures containing ASO, HF, and HF-agent complex, a reduction in the molar ratio of HF per Lewis base site of a complexing agent decreases the solubility of ASO in the HF-agent complex. Mixtures of ASO, HF, and HF-pyridine complex provide a good example of this phenomenon. A reduction in the molar ratio of HF per pyridine in a mixture containing ASO, HF, and HF-pyridine complex decreases the solubility of ASO in the HF-pyridine complex. A person of ordinary skill in the art would, therefore, try to separate a mixture of ASO, HF, and pyridine, by first removing HF until the remaining mixture of HF and pyridine is immiscible in ASO, and then removing the ASO by effecting the phase separation. Unlike the prior art processes, the present invention removes ASO, and light ASO in particular, along with the HF and does not rely on only phase separation to remove ASO. Although persons of ordinary skill in the art believed that removal of any ASO with the HF prior to phase separation was a disadvantage, this invention turns this apparent disadvantage into an advantage by using the existing alkylate product fractionator to separate the ASO from the HF and thereby to maximize rejection of ASO from the process.

Accordingly, in a broad embodiment this invention is a hydrocarbon alkylation process that uses a catalytic mixture containing an HF-agent complex in an alkylation zone and that produces an acid soluble oil (ASO) by-product. The HF-agent complex is formed from a complexing agent that contains at least one Lewis base site containing a Group 5A element. In this invention, the ASO is rejected from the process and the HF-agent complex is recovered and recycled to the alkylation zone. A hydrocarbon substrate is alkylated with a hydrocarbon alkylation agent in the presence of HF and HF-agent complex in an alkylation zone. A reactor effluent stream containing alkylate and ASO is produced in the alkylation zone. The reactor effluent stream is separated into an acid effluent stream containing ASO, HF, and HF-agent complex and a hydrocarbon effluent stream containing alkylate. A by-product stream is formed from at least a portion of the acid effluent stream. The by-product stream contains ASO, HF, and HF-agent complex and has a molar ratio of HF per Lewis base site substantially above 5:1. A portion of the HF and a portion of the ASO is selectively removed from the by-product stream to produce an HF-enriched stream containing HF and ASO and an HF-depleted stream. The HF-depleted stream contains ASO, HF, and HF-agent complex and has a molar ratio of HF per Lewis base site of 3:1 to 5:1. The HF-depleted stream is separated into a hydrocarbon phase enriched in ASO and an acid phase depleted in ASO that contains a substantial portion of the HF-agent complex. At least a portion of the hydrocarbon effluent stream and at least a portion of the HF-enriched stream is passed to a fractionation zone. A recycle stream containing HF and a product stream containing alkylate and ASO is recovered from the fractionation zone. At least a portion of the acid phase and at least a portion of the recycle stream are recycled to the alkylation zone. The hydrocarbon phase is rejected from the process.

BRIEF DESCRIPTION OF THE DRAWINGS

The drawing is a flow diagram of a preferred embodiment of the invention.

DETAILED DESCRIPTION OF THE INVENTION

This invention is directed toward an improvement in a process for the alkylation of a hydrocarbon substrate with a hydrocarbon alkylation agent. Suitable substrates, such as isoparaffins and aromatics, and alkylation agents, such as olefins, are those that are known in the art to be suitable for motor fuel alkylation and detergent alkylation, such as those taught in U.S. Pat. No. 4,239,931 (motor fuel) and U.S. Pat. No. 4,503,277 (detergent), the teachings of which are incorporated herein by reference. U.S. Pat. Nos. 4,239,931 and 4,503,277 also teach apparatus and conditions that are suitable for use in this invention for the alkylation reaction, the separation of the alkylation reaction effluent into an acid effluent stream and a hydrocarbon effluent stream, and separation of the product alkylate from hydrocarbon substrate and other hydrocarbons in the hydrocarbon effluent stream. As taught in U.S. Pat. No. 5,073,674, the mixture that catalyzes the alkylation reactions in this invention is a mixture of HF and HF-agent complex. The alkylation reaction effluent also contains ASO by-product. Thus, ASO, HF, and complexing agent are present in the acid effluent stream as well in that portion of the acid effluent stream, which is called herein the by-product stream, that is regenerated according to the method of this invention.

ASO, as mentioned previously, is a recognized term in the art of alkylation. ASO is formed in both a motor fuel alkylation process and a detergent alkylation process. In alkylation processes, ASO is an alkylation by-product that is generally formed by oligomerization of reactants or by reactions of impurities in the charge stock to the alkylation process. As such, ASO may have a variety of different compositions and physical properties depending on the reactants charged to the alkylation process, the operating conditions, etc. It may contain non-hydrocarbon elements, including halogens, oxygen, nitrogen, sulfur, etc. ASO may be in the boiling range of from about 149 to about 482° C. (300 to 900° F.). ASO that has a boiling range similar to that of alkylate of from about 212 to about 450° F. (100 to 232° C.) is referred to herein as light ASO, while ASO that has a boiling range of from about 450° F. to about 900° F. (232 to 482° C.) is referred to herein as heavy ASO. The concentration of ASO in the by-product stream is generally between 0.5 and 25 wt-%.

The complexing agent contains a Lewis base site. Suitable Lewis bases that can function as complexing agents contain any one of the Group 5A elements, namely nitrogen, phosphorous, arsenic, antimony, and bismuth. When the molar ratio of HF per Lewis base site is reduced sufficiently, the HF-agent complex becomes sufficiently polar that it is not very soluble in ASO, which is generally non-polar. Thus, the HF-agent complex and ASO are then separable by phase separation. The more polar the HF-agent complex, the more facile is the separation between the HF-agent complex and the ASO. The preferred Group 5A element is nitrogen. The complexing agents containing nitrogen can be: one of the chemical formula $NR_1R_2R_3$, where $R_1$, $R_2$, and $R_3$ can be alkyl, aryl or hydrogen, including ammonia, methylamine, ethylamine, propylamines, butylamines, pentylamines, dimethylamine, trimethylamine, diethylamine, triethylamine, diphenylamine, dibenzylamine, and aniline and alkyl- and aryl-substituted anilines including N,N-dimethylaniline; pyridine, and alkyl- and aryl- substituted pyridines, especially methyl-substituted pyridines, including picolines, lutidines, and collidine; a polycyclic compound, such as quinoline; a compound having more than one nitrogen atom, including noncyclic compounds such as ethylenediamine and cyclic compounds such as imidazoles and polyvinyl-pyridine; and a cyclic compound having other kinds of atoms such as oxygen in the ring, including morpholine. The complexing agent may contain more than one Lewis base site. Among the complexing agents containing nitrogen, the preferred complexing agent is a heterocyclic hydrocarbon compound having nitrogen in the ring as a heteroatom. The preferred complexing agent is pyridine. The by-product stream may contain more than one complexing agent. The description of the invention that follows focuses principally on the use of pyridine as a complexing agent, but this description is not intended to limit the scope of this invention as set forth in the claims.

In a mixture with HF, the Lewis base site may complex with HF to varying degrees. The extent of complexing depends in part on the type of Lewis base site and the molar ratio of HF per Lewis base site. A mixture comprising HF and a complexing agent comprising a Lewis base site may be comprised of several HF-agent complexes, each having a different number of HF molecules per Lewis base site. Thus, it is to be understood that the term "HF-agent complex" refers to one or more HF-agent complexes. The ease of phase separation of the complexing agent from the ASO may depend on the actual HF-agent complex that is present in the mixture, rather than on the Lewis base site itself.

In the present invention, the concentration of complexing agent in the by-product stream is generally between 1 and 50 wt-% on an ASO-free basis, and the concentration of HF in the by-product stream is generally between 50 and 99 wt-% on an ASO-free basis. This typically corresponds to a molar ratio of HF per Lewis base site substantially in excess of 5:1. Where the complexing agent is pyridine, the concentration of pyridine in the by-product stream is generally from 5 wt-% to 25 wt-% on an ASO-free basis, and preferably from 10 wt-% to 19 wt-% on an ASO-free basis. Accordingly, for pyridine the concentration of HF in the by-product stream is generally from 75 wt-% to 95 wt-% on an ASO-free basis, and preferably from 81 wt-% to 90 wt-% on an ASO-free basis. In terms of molar ratio of HF per pyridine, the by-product stream is generally from 12:1 to 75:1 and preferably from 17:1 to 35:1.

In accord with this invention, first at least a portion of the HF and the ASO in the by-product stream is removed. Some pyridine, perhaps complexed with HF, may also be removed but this is preferably minimized. The particular method of removing the HF and the ASO from the by-product stream is not an essential feature of this invention and may include flashing, distillation, or extraction, but is preferably stripping. Suitable stripping arrangements are known in the art. See, for example, U.S. Pat. No. 3,249,650 where isobutane is introduced into the bottom of a stripping column, commonly called a regenerator. The regenerator may be a flash chamber, packed bed column, or trayed column. The heat for the separation may be provided by a reboiler, via the stripping medium, or by preheating the by-product stream. The stripping medium, if used, may be nitrogen, hydrogen, methane, ethane, propane, isobutane, pentane, benzene, or another compound that does not react with the by-product stream at stripping conditions.

It is an essential feature that the stream that remains after the removal of HF and ASO from the by-product stream, which is referred to herein as the HF-depleted stream, contains an HF per complexing agent mole ratio of 3:1 to 5:1. In the HF-depleted stream, the concentration of HF is generally between 20 and 80 wt-% on an ASO-free basis. Where the complexing agent is pyridine, the concentration of HF in the HF-depleted stream is generally between 40 wt-% and 70 wt-% on an ASO-free basis, and preferably between 43 and 65 wt-% on an ASO-free basis. Within these ranges, the lower the concentration of HF, the more facile is the subsequent separation of the HF-pyridine complex from the ASO, but the higher are the capital and operating costs of the stripping.

It is also an essential feature of this invention that the stream that contains the removed HF, which is referred to herein as the HF-enriched stream, also contains ASO. In the HF-enriched stream, the concentration of HF on a water-free basis is generally between 80 and 99 wt-% and preferably between 85 and 90 wt-%, and the concentration of ASO on a water-free basis is generally between 1 and 20 wt-% and preferably between 10 and 15 wt-%. If water is present in the HF-enriched stream, the concentration of water is generally between 0.5 and 15.0 wt-% and preferably less than 7.0 wt-%.

The process conditions under which HF and ASO are removed from the by-product stream include temperatures in the range of from 10 to 260° C. (50 to 500° F.), with 52 to 232° C. (125 to 450° F.) being preferred, and pressures in the range of from 138 to 1724 kPa (20 to 250 psi), with 586 to 1379 kPa (85 to 200 psi) being preferred. The process conditions are not sufficient to destroy the HF-pyridine complex, which remains in existence and present in the stripping column bottoms product, or HF-depleted stream. By "destroying" the HF-pyridine complex, it is meant the termination of interaction between HF and pyridine molecules that produces a complex, as evidenced by the properties of complexes described in Olah and Oda et al. In other words, when the HF-pyridine complex is destroyed, either the HF and the nitrogen of the pyridine interact and exhibit the properties of an ammonium fluoride salt, or the HF and the pyridine do not interact and each exhibits its properties as a pure substance. Merely reducing the molar ratio of HF per pyridine of a stream containing an HF-pyridine complex does not necessarily destroy the complex. Thus, the fact that the molar ratio of HF per pyridine of the stripping column bottoms product is less than the molar ratio of HF per pyridine of the HF-pyridine complex in the stripping column feed does not necessarily mean that the stripping destroyed the complex. It is believed that reducing the stripping temperature and minimizing the exposure of the complex to elemental iron decreases the likelihood that the complex will be destroyed during stripping.

The stripping column bottoms product, or HF-depleted stream, is passed to a zone for separating the ASO from the HF-pyridine complex. The preferred method of separation employs differences in density or miscibility or both to separate the HF-depleted stream into an ASO-enriched hydrocarbon phase and a HF-pyridine-complex-enriched acid phase. In an alkylation process, the ASO-enriched hydrocarbon phase is rejected from the process, and the HF-pyridine-complex-enriched acid phase is recycled to the alkylation zone. The concentration of complexing agent in the ASO-enriched hydrocarbon phase is generally between 0.1 and 5 wt-%, but preferably the concentration is between 0.1 and 1.0 wt-%. In an alkylation process employing pyridine, the lower the concentration of pyridine in the ASO-enriched phase, the lower is the quantity of pyridine that is lost from the process, because the ASO-enriched phase is generally rejected from the process. The concentration of pyridine in the ASO-enriched hydrocarbon phase is generally not controlled directly but is instead determined indirectly by setting other operating variables such as the molar ratio of HF per pyridine of the stripping column bottoms product. The concentration of ASO in the HF-amine-complex-enriched acid phase is generally between 0.1 and 50 wt-%. Where the complexing agent is pyridine, the concentration of ASO in the HF-pyridine-complex-enriched phase is generally between 0.1 wt-% and 25 wt-%, and preferably the concentration is between 0.1 and 15 wt-%. In an HF alkylation process employing pyridine, the lower the concentration of ASO in the HF-pyridine-complex-enriched phase, the lower the amount of ASO that is recycled to the alkylation process. Reducing the concentration of ASO that is recycled to an HF alkylation process is desirable.

The process conditions under which the HF-depleted stream is separated into an ASO-enriched hydrocarbon phase and an HF-agent-complex-enriched acid phase include temperatures in the range of from −18 to 260° C. (0 to 500° F.) with 149 to 260° C. (300 to 500° F.) being preferred when the ASO has been formed in a detergent alkylation process. A temperature of 66 to 149° C. (150 to 300° F.) is preferred when the ASO has been formed in a motor fuel alkylation process. Pressures in the range of from 138 to 1724 kPa (20 to 250 psi), preferably with the pressure being sufficient to minimize or prevent vaporization and to maintain the streams in a liquid phase.

The concentration of ASO in the HF-pyridine-complex-enriched acid phase can be further reduced by stripping the HF-pyridine-complex-enriched acid phase again to remove more HF, and then separating by phase separation into two streams. By successive stripping and settling, the concentration of ASO in the HF-pyridine-complex-enriched acid phase can be reduced to levels below 1.0 wt-%. The process conditions for successive stripping and settling steps are generally those described previously for stripping the by-product stream and settling the HF-depleted stream.

In accord with this invention, the HF-enriched stream passes to the alkylate product fractionator. The alkylate product fractionator is often called an isostripper in a motor fuel alkylation process and a product stripper in a detergent alkylation process. In addition to its usual function of separating the alkylate from the substrate and other hydrocarbons in the hydrocarbon effluent stream, the alkylate product fractionator in this invention separates the ASO from the HF in the hydrocarbon effluent stream. A net overhead stream from the product fractionator containing HF and less than 2.0 wt-% ASO is recycled to the alkylation reactor, and a bottom stream containing ASO is removed from the process.

The following description of this invention is presented with reference to the drawing, which shows a preferred embodiment of the invention. The drawing is a process flow diagram in which details such as pumps, instrumentation and controls, quench systems, heat exchangers, valves, and other equipment that are not essential to an understanding of the invention are omitted. Persons of ordinary skill in the art are aware of and are able to provide the equipment that has been omitted from the drawing.

The drawing shows a commercial process for the alkylation of isobutane with a mixture of olefins including propylene, butylenes, and amylenes to produce a full boiling range, normally-liquid alkylate. The alkylation occurs in the presence of HF, pyridine, and HF-pyridine complex. The olefinic mixture enters the process through a line 12 and combines with an isobutane-containing recycle stream that flows through a line 48. This stream of olefins and recycle isobutane flows through a line 16 and combines with make-up isobutane that enters the process through a line 14. The combined stream of olefins, recycle isobutane, and make-up isobutane flows through a line 18 and constitutes the feed stream to the alkylation zone 10. The alkylation zone 10 is a well-known design that has multiple feed injection points and a heat exchanger, which are not shown in drawing.

In addition to the feed stream, a stream that contains HF, pyridine, and HF-pyridine complex is introduced to the alkylation zone 10 through a line 22. This stream in the line 22 may also contain ASO, but it is an objective of this invention to minimize the concentration of ASO in this stream. The stream in the line 22 is formed by combining five HF-containing streams: a portion of the acid phase from the effluent settler 20 that flows through lines 62, 64, 66, 68, and 72; a portion of the acid phase from isostripper overhead acid boot 45 that flows through lines 44, 64, 66, 68, and 72; the overhead stream of external regenerator 60 that flows through lines 76 and 72; a portion of the acid phase from the pyridine stripper overhead acid boot 105 that flows through lines 102, 106, and 24; and the acid phase from the pyridine stripper bottom settler 90 that flows through lines 116, 68, and 72. These five streams, which are described in more detail below, combine in line 22 and flow into alkylation zone 10.

The effluent of the alkylation zone 10 passes through a line 26 to the effluent settler 20. The effluent generally contains product alkylate, ASO by-product, unreacted isobutane, HF, and HF-pyridine complex. The effluent will also contain normal butane and propane, if any, that entered the process through line 12 with the stream of olefins and which tend to be nonreactive in the alkylation zone 10. In the effluent settler 20, the alkylation zone effluent gravitationally separates into a hydrocarbon effluent stream that contains the product alkylate, isobutane, normal butane, and propane and an acid effluent stream that contains ASO, HF, and HF-pyridine complex. The hydrocarbon effluent stream is withdrawn from the effluent settler 20 through a line 28 and the acid effluent stream is withdrawn through a line 62.

The hydrocarbon effluent stream in line 28 combines with a portion of the acid phase from the pyridine stripper overhead acid boot 105 flowing through a line 107 to form a fractionator feed stream that flows through line 32 to the product alkylate fractionator 30, which is referred to hereinafter as the isostripper. The fractionator feed stream enters the isostripper 30 generally at an upper point of the isostripper 30. As used herein, the term "upper point" is intended to indicate a point in the fractionation column which is separated from the top end of the column by less than eight fractionation trays. The acid phase flowing in line 107 contains HF and ASO, as will be explained in more detail hereinafter, and the flow rate of HF in the acid phase through line 107 is not in excess of the amount of HF that is soluble in the hydrocarbons present in the isostripper 30 at the operating conditions of the isostripper 30. In the isostripper 30, the fractionator feed stream is separated into a bottom stream containing alkylate product and ASO in line 31, a first sidecut stream containing isobutane in line 46, a second sidecut stream containing normal butane in line 34, and an overhead stream containing HF, isobutane, and propane in line 36. The first sidecut stream is removed from the isostripper 30 at a first intermediate point below the feed point of the isostripper 30. As used herein, the term "intermediate point" and similar terms is intended to indicate a point in the fractionation column which is separated from each end of the column by at least three fractionation trays. The number of trays separating the feed point and the first intermediate point should be sufficient to insure that the liquid present at the first intermediate point in the isostripper 30 has a very low concentration of propane. The second sidecut stream is removed from the isostripper 30 at a second intermediate point below the first intermediate point. The number of trays separating the first intermediate point and the second intermediate point should be sufficient to insure that the liquid present at the second intermediate point in the isostripper 30 has a very low concentration of isobutane, and the number of trays separating the second intermediate point and the bottom of the isostripper 30 should be sufficient to insure that the liquid present at the second intermediate point in the isostripper 30 has a very low concentration of the product alkylate. The isostripper bottom stream and the second sidecut stream are recovered from the process. The first sidecut stream combines with a stream flowing in line 58, which is described hereinafter, and the combined stream is recycled to the alkylation zone 10 through lines 48, 16, and 18.

The isostripper overhead stream in line 36 is typically cooled in a heat exchanger (not shown) and passes to an overhead receiver 40 that has an attached acid boot 45. In receiver 40 and boot 45, the overhead stream separates by phase separation into a hydrocarbon stream containing isobutane and propane that exits through line 38 and an acid stream containing HF that exits through line 44. The concentration of ASO on a water-free basis is generally less than 5 wt-% in the acid stream flowing in line 44. A portion of the overhead hydrocarbon stream is passed as reflux to isostripper 30 through a line 42 and the remainder passes through a line 52 to depropanizer 50. In depropanizer 50, the entering isobutane and propane are separated into a depropanizer overhead stream containing propane that exits through a line 54 and is recovered from the process and a depropanizer bottom stream containing isobutane that exits through a line 56. The depropanizer bottom stream combines with a portion of the hydrocarbon stream in line 108 from the pyridine stripper overhead receiver 100, which is described hereinafter, and is recycled to the alkylation zone 10 through lines 58, 48, 16, and 18.

The by-product stream is formed from a portion of the combined acid stream from the effluent settler 20 and the isostripper overhead boot 45 that flows through the line 64. The by-product stream is that portion of the combined stream in line 64 that flows through line 74 to the regenerator 60. The by-product stream contains ASO, HF, and HF-pyridine complex. In the regenerator 60, the by-product stream is stripped with isobutane (not shown) that is introduced at a lower point of the regenerator 60. In the regenerator 60, HF is selectively removed from the by-product stream in an HF-enriched overhead stream containing isobutane through lines 76, and returns to the alkylation zone 10 through lines 72 and 22. The bottoms stream of the regenerator 60 is depleted in HF and is passed through a line 78 to a gravity settler 70. In the gravity settler 70, the bottoms stream of the regenerator 60 separates by phase separation into a settler overhead phase enriched in ASO and a settler bottoms phase enriched in the HF-pyridine complex. The settler overhead phase is passed through a line 82 to facilities that neutralize and dispose of the ASO.

The settler bottoms phase is passed through a line 84 to a pyridine stripper 80. In the pyridine stripper 80, HF and ASO are selectively removed from the settler bottoms phase under conditions selected to result in a mole ratio of HF per pyridine of 3:1 to 5:1 in the bottom stream of the pyridine stripper 80. The ASO that is stripped overhead in the pyridine stripper 80 tends to be light ASO, as distinguished from heavy ASO that tends to be recovered in the pyridine stripper bottom stream. The bottoms stream of the pyridine stripper 80, which is referred to herein as the HF-depleted stream, is passed through a line 112 to a gravity settler 90. In the gravity settler 90, the HF-depleted stream separates by phase separation into a settler overhead phase enriched in ASO and a settler bottoms phase enriched in the HF-pyridine complex. The settler overhead phase is passed through a line 114 to neutralization and disposal facilities. The settler bottoms phase is passed through the line 116 and returns to the alkylation zone 10 as described previously.

The pyridine stripper overhead stream in line 86 is typically condensed in a heat exchanger (not shown) and then passed to an overhead receiver 100 that has an attached acid boot 105. The pyridine stripper overhead stream contains HF, ASO, and isobutane. In overhead receiver 100, the overhead stream separates into a hydrocarbon stream containing isobutane that exits through line 88 and an acid stream containing HF and ASO that exits through line 102. When valve 92 in line 94 is open, a portion of the hydrocarbon stream may be passed as reflux to the pyridine stripper 80 through lines 94 and 96. That portion of the overhead hydrocarbon stream that is not refluxed to the pyridine stripper 80 passes through the line 108, combines with the depropanizer bottoms stream in the line 56, and is recycled to the alkylation zone 10 as described previously. Similarly, when valve 98 in line 104 is open, a portion of the acid stream may be passed as reflux to the pyridine stripper 80 through lines 104 and 96, and any portion of the acid stream that is not used as reflux passes through line 106. A portion of the acid stream flowing in line 106 passes through line 107, combines with the hydrocarbon effluent stream flowing in line 28, and flows through line 32 into isostripper 30, where the ASO is recovered from the bottom of isostripper 30 and the HF is recovered from the acid boot 45. The remaining portion of the acid stream in line 107 that is not passed to the isostripper 30 is recycled to the alkylation zone 10 as described previously.

There are a number of possible variations on the preferred flow scheme in the drawing. In a first variation, rather than selectively stripping a sufficient amount of HF in the regenerator 60 to effect a phase separation in gravity settler 70, it is possible to strip an insufficient amount of HF and, accordingly, a settler overhead phase either is not withdrawn from the gravity settler 70 or is withdrawn only intermittently. In a second variation, rather than two separate columns such as regenerator 60 and pyridine stripper 80 for selective HF stripping, it is possible for a single column to selectively strip a sufficient amount of HF from the by-product stream to produce a bottom stream having an molar ratio of HF per complexing agent of 3:1 to 5:1. The overhead stream of that single column would contain not only HF but also ASO, and at least a portion of the acid phase recovered from that overhead stream would be passed to the isostripper 30. In a third variation, rather than selectively stripping overhead only HF in the regenerator 60, it is possible to strip overhead in the regenerator 60 both HF and ASO. In this third variation, the regenerator overhead stream would be condensed in a manner similar to that shown in the drawing for the pyridine stripper overhead stream, and at least a portion of the acid phase recovered from the regenerator overhead stream would be passed to the isostripper 30.

What is claimed is:

1. A hydrocarbon alkylation process using a catalytic mixture containing an HF-agent complex in an alkylation zone, wherein the HF-agent complex is formed from a complexing agent containing at least one Lewis base site containing a Group 5A element, and producing an acid soluble oil (ASO) by-product wherein ASO is rejected from the process and the HF-agent complex is recovered and recycled to the alkylation zone by the steps of:

a) alkylating a hydrocarbon substrate with a hydrocarbon alkylation agent in the presence of HF and HF-agent complex in an alkylation zone and producing a reactor effluent stream containing alkylate and ASO;

b) separating the reactor effluent stream into an acid effluent stream containing ASO, HF, and HF-agent complex and a hydrocarbon effluent stream containing alkylate;

c) forming a by-product stream from at least a portion of the acid effluent stream, wherein the by-product stream contains ASO, HF, and HF-agent complex and the by-product stream has a molar ratio of HF per Lewis base site substantially above 5:1;

d) selectively removing a portion of the HF and a portion of the ASO from the by-product stream to produce an HF-enriched stream containing HF and ASO and an HF-depleted stream, wherein the HF-depleted stream contains ASO, HF, and HF-agent complex and has a molar ratio of HF per Lewis base site of 3:1 to 5:1;

e) separating the HF-depleted stream into a hydrocarbon phase enriched in ASO and an acid phase depleted in ASO and containing a substantial portion of the HF-agent complex;

f) passing at least a portion of the hydrocarbon effluent stream and at least a portion of the HF-enriched stream to a fractionation zone and recovering from the fractionation zone a recycle stream containing HF and a product stream containing alkylate and ASO;

g) recycling at least a portion of the acid phase and at least a portion of the recycle stream to the alkylation zone; and h) rejecting the hydrocarbon phase from the process.

2. The process of claim 1 wherein a first aliquot portion of the HF-enriched stream passes to the fractionation zone, and further characterized in that a second aliquot portion of the HF-enriched stream is passed to the alkylation zone.

3. The process of claim 1 wherein in Step (d) the HF is selectively removed by stripping.

4. The process of claim 1 wherein in Step (e) the HF-depleted stream is separated by gravitational settling.

5. The process of claim 1 wherein the by-product stream has a molar ratio of HF per Lewis base site substantially above 17:1, and further characterized in that (i) a portion of the HF from the by-product stream is selectively stripped to produce an intermediate stream enriched in HF and an HF-stripped stream having a molar ratio of HF per Lewis base of 6:1 to 17:1 and (ii) a portion of the HF is selectively stripped from the HF-stripped stream to produce the HF-depleted stream.

6. The process of claim 5 further characterized in that (i) the HF-stripped stream is separated by gravitational settling into a first intermediate phase enriched in ASO and a second intermediate phase depleted in ASO and containing HF and a substantial portion of the HF-agent complex and (ii) a portion of the HF is selectively stripped from the second intermediate phase to produce the HF-depleted stream.

7. The process of claim 5 wherein in Step (e) of claim 1 the HF-depleted stream is separated by gravitational settling.

8. The process of claim 5 wherein the intermediate stream contains ASO, and further characterized in that (i) a first aliquot portion of the intermediate stream is passed to the alkylation zone and (ii) a second aliquot portion of the intermediate stream is passed to the fractionation zone.

9. The process of claim 5 wherein a first aliquot portion of the HF-enriched stream passes to the fractionation zone, and further characterized in that a second aliquot portion of the HF-enriched stream is passed to the alkylation zone.

10. The process of claim 1 wherein the complexing agent is a heterocyclic hydrocarbon compound having nitrogen in the ring as a heteroatom.

11. The process of claim 10 wherein the heterocyclic hydrocarbon compound is pyridine.

12. The process of claim 1 further characterized in that the HF-enriched stream has a concentration of ASO of more than 1 wt-%.

13. The process of claim 1 further characterized in that the ASO in the HF-enriched stream has a boiling range of from about 212 to about 450° F.

14. The process of claim 1 further characterized in that the acid phase has a concentration of ASO of less than 1 wt-%.

15. The process of claim 1 further characterized in that the recycle stream has a concentration of ASO of less than 2.0 wt-%.

* * * * *